Figure 1:
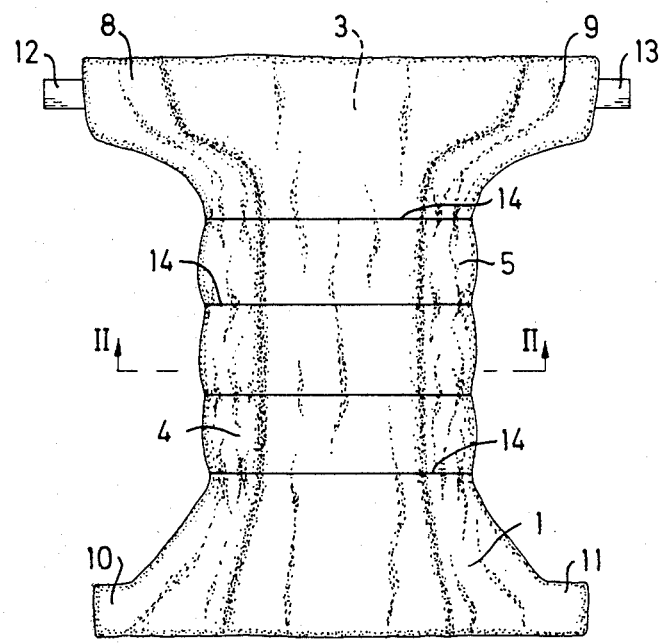

United States Patent [19]

Ternström et al.

[11] 4,323,070
[45] Apr. 6, 1982

[54] DISPOSABLE DIAPER

[75] Inventors: Ingela M. Ternström, Göteborg; Lars E. Boman, Mölndal, both of Sweden

[73] Assignee: Molnlycke AB, Goteborg, Sweden

[21] Appl. No.: 116,808

[22] Filed: Jan. 30, 1980

[30] Foreign Application Priority Data

Feb. 2, 1979 [SE] Sweden ............................. 7900938

[51] Int. Cl.$^3$ ........................................... A41B 13/02
[52] U.S. Cl. ............................................... 128/287
[58] Field of Search .............. 128/284, 286, 287, 288, 128/290 H

[56] References Cited

U.S. PATENT DOCUMENTS 2,062,594 12/1936 McNair .
2,866,459 12/1958 Sobelson .
3,236,238 2/1966 Morse .
3,481,337 12/1969 Ruffo .
3,995,637 12/1976 Schaar ............................... 128/284
4,226,238 10/1980 Bianco ............................... 128/287

FOREIGN PATENT DOCUMENTS 1203705 10/1965 Fed. Rep. of Germany .
2712069 10/1977 Fed. Rep. of Germany .

*Primary Examiner*—C. Fred Rosenbaum
*Attorney, Agent, or Firm*—Young & Thompson

[57] ABSTRACT

A disposable diaper including a first outer layer of a liquid-permeable material intended to abut the body of the user, a second outer layer of a liquid-impermeable material and an intermediate layer of absorbent material arranged between said two outer layers. At least that portion of the diaper, which is situated in the user's crotch, is provided with elastic bands or threads extending between the two side edges of the diaper, these bands or threads being at least partially connected with pretension to the liquid-permeable outer layer.

3 Claims, 5 Drawing Figures

DISPOSABLE DIAPER

The present invention relates to a disposable diaper of the kind comprising a first outer layer of a liquid-permeable material intended to abut the body of the person using said diaper, a second outer layer of a liquid-impermeable material and an intermediate layer of absorbent material arranged between the two aforementioned outer layers.

Such a disposable diaper providing sufficient security against transverse leakage of urine and faeces at the same time as it is comfortable has not yet been successfully manufactured.

In previously known diapers, attempts have been made to prevent urine and faeces leakage by means of arranging elastic bands or threads along and near the two side edges of the diaper. These bands or threads are intended to hold the diaper side edges firmly against the user's body. However, they have been burdened by the disadvantage of having to be tightly stretched when the diaper is used, resulting in their heavily chafing the user's skin.

Another disadvantage is that said known disposable diaper is much too tight. The skin enclosed by the diaper cannot "breathe" and becomes irritated.

Furthermore, the arrangement of longitudinal elastic bands or threads along and near the side edges also causes the known diaper to contract and form a large bag in the vicinity of the user's crotch. This is both irritating and gives the diaper a clumsy and unappealing appearance.

By means of the present invention, a diaper of the kind mentioned in the preamble has been developed which eliminates the abovementioned disadvantages.

According to the invention, said disposable diaper is characterized in that at least that part of the diaper which is intended to be situated in the user's crotch is provided with elastic bands or threads extending between said diaper's two longitudinal side edges. Said bands or threads are prestretched and at least partially connected to the liquidpermeable outer layer.

The elastic threads or bands extending between the two side edges cause the diaper to contract and provide the middle section of said diaper with a bowl-like shape. This prevents transverse leakage of urine and faeces at the same time as it allows air exchange.

The invention shall be described in more detail below, reference being made to the three different embodiments shown in the enclosed drawings.

Figure 2:
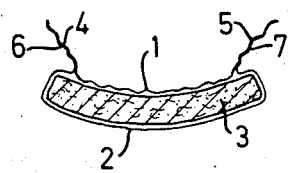
Figure 3:
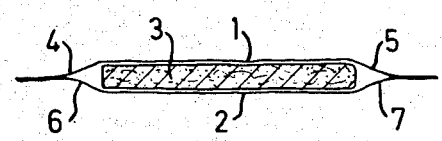
Figure 4:
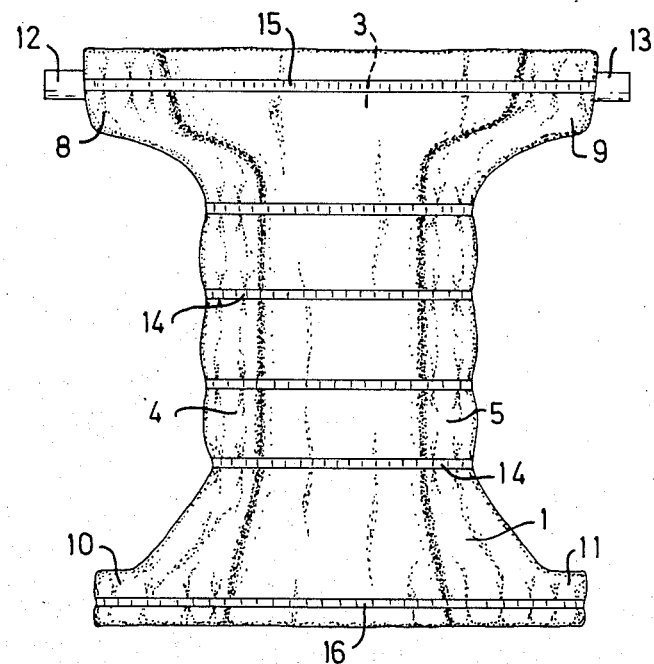
Figure 5:
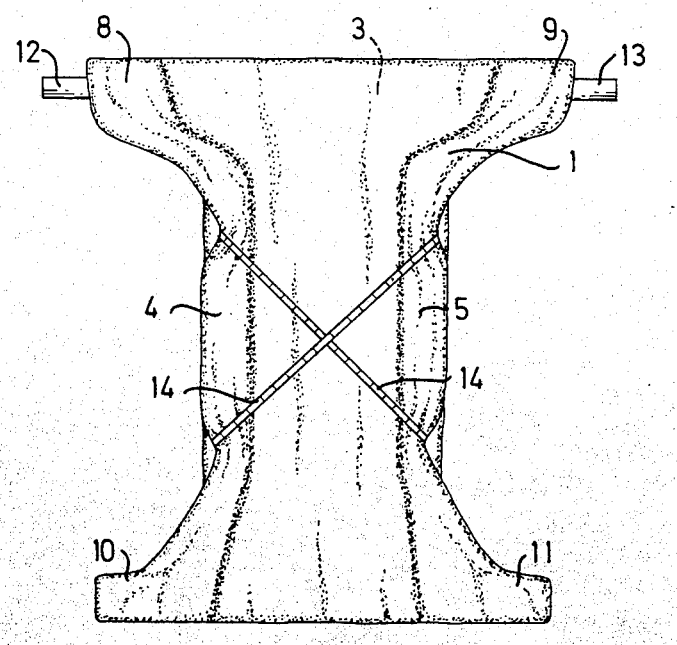

FIG. 1 in said drawings is a plan view of the inside of a diaper according to the first embodiment, FIG. 2 is a cross-section along the line II—II in FIG. 1, FIG. 3 is the section according to FIG. 2 when the diaper is stretched in its transverse direction, FIG. 4 is a plan view of the inside of a diaper according to the second embodiment, while FIG. 5 is a plan view of the inside of a diaper according to the third embodiment.

As can be seen in the drawings, a disposable diaper according to the present invention comprises a first outer layer 1 of a liquid-permeable material, for example a nonwoven textile, a second outer layer 2 of a liquid-impermeable material, for example polyethylene, and an absorbent intermediate layer 3 which is enclosed by the two outer layers.

Sections 4, 5; 6, 7 of the two outer layers 1, 2 extend transversely a distance beyond the absorbent intermediate layer or core 3. They are provided with extensions 8–11 at both ends of the diaper, said extensions being intended to be fastened around the user's waist. Tape tabs 12,13 are arranged on two of said extensions 8,9 to serve as means of fastening the diaper.

Elastic threads 14 are arranged on the liquid-permeable layer 1 at a mutual distance from each other at least within the central portion of the diaper and between said diaper's two longitudinal side edges. Said threads 14 are arranged on the outer layer 1 in a pre-strectched state and are connected to said layer by means of binder.

By means of the elastic threads 14 being applied to the liquid-permeable outer layer 1 in a pre-tensioned, that is stretched, state when the diaper is being produced the finished diaper is pulled together transversely, its middle section obtaining a bowl-like shape which, when the diaper is being used, is situated in the user's crotch. This is well illustrated in FIG. 2. More precisely, the threads 14 pull together the liquid-permeable outer layer 1 which, in turn, pulls together sections 6,7 of the liquid-impermeable layer 2 around the absorbent layer or absorption core 3 edges. This is also illustrated in FIG. 2.

A cross-section of the diaper is shown in FIG. 3. The two outer layers 1 and 2 are stretched out in the transverse direction of the diaper. In this state, the elastic threads 14 are stretched. As can be seen in FIG. 3, the sections 4,6; 5,7 of the two outer layers 1,2 projecting from both sides of the intermediate layer or absorption core 3 are only joined together along their outer edges.

The production of a disposable diaper according to the invention takes place in a continuous sheet, the elastic threads being stretched in the longitudinal direction of said sheet. When the sheet is cut so as to form separate diapers, said diapers contract in the transverse direction so as to assume the shape revealed in FIG. 2. The liquid-impermeable layer 2 is hereby arranged around the side edges of the intermediate layer or the absorbent core 3 without it having to be folded up around the same during manufacture. The sections of the liquid-impermeable layer situated around the edges of said intermediate layer effectively prevent all transverse leakage from the diaper.

By means of the two outer layers 1,2 being stretched around the intermediate layer 3 by means of the elastic threads 14, shape stability of said intermediate layer will increase.

FIG. 2 illustrates how, as a result of the pretensioning or stretching of the elastic threads, the sections of the outer layers 1,2, which are situated on both sides of the diaper, will also fold. This contributes to preventing transverse leakage and causes the liquid-permeable outer layer consisting of non-woven material to abut the skin of the user.

When the elastic threads 14 contract the liquid-permeable outer layer 1, said layer also folds in its longitudinal direction. Said folding is illustrated in FIG. 2 and has the advantage that faeces and urine will spread in the longitudinal direction of the diaper rather than in its transverse direction. Furthermore, the fold in question entails that when the diaper is used, the absorbent core and the body of the user are held at a distance from one another. Thus, the user remains substantially dry, even when the absorbent core in the diaper is saturated with urine.

In FIGS. 4 and 5, those parts corresponding to similar details in FIG. 1 have been provided with the same reference numerals. However, the elastic threads in FIG. 1 have been replaced by elastic bands 14 in the two embodiments shown in FIGS. 4 and 5.

In the embodiment shown in FIG. 4, the two ends of the diaper have also been provided with transverse elastic bands 15,16. These further bands are intended to stretch the diaper around the waist of the user. In this manner, the diaper has a better fit at the same time as leakage is prevented around the user's waist. Naturally, the elastic bands 15 have the same function as the threads 14 in the embodiment shown in FIG. 1.

The elastic bands 14 in the embodiment shown in FIG. 5 are arranged so as to cross each other. In this manner, essentially the same effects described in connection with the embodiment shown in FIGS. 1 and 2 are obtained. By means of the crossed bands also contracting the diaper in the longitudinal direction, a diaper according to said embodiment has a more pronounced bowl shape than the diaper according to the embodiment shown in FIGS. 1-3.

The invention is not restricted to the above-described embodiments shown in the drawings. Rather, they can be modified in different ways within the scope of the claims.

For example, the elastic threads or bands 14 do not have to be connected to a premanufactured non-woven layer. They can be affixed to a web of loose fibres so as to thereafter be united with the same when a binder is added, by means of which binder the loose fibres are united into a non-woven fibre layer.

The liquid-permeable outer layer can also consist of two non-woven layers, between which the elastic bands or threads are arranged. Not all of the bands or threads need to be connected to the liquid-permeable layer with the same pretension or degree of stretching. By means of varying pretension with the different bands or threads in the middle section of the diaper, said diaper can be provided with a certain desired bowl-shape.

What we claim is:

1. In a disposable diaper comprising a first outer layer of a liquid-permeable material and intended to abut the user's body, a second outer layer of a liquid-impermeable material and an intermediate layer of absorbent material arranged between said two outer layers; the improvement in which at least that portion of the diaper situated in the user's crotch is provided with elastic band or thread means extending between the two side edges of the diaper, said band or thread means being at least partially connected with pretension to the liquid-permeable layer and arranged prestressed on the liquid-permeable layer in order to preform said portion of the diaper to a bowl-like shape, whereby in use the marginal regions of the diaper in said crotch portion are forced against the user's body and thereby prevent lateral leakage, the parts of the two outer layers situated in the user's crotch extending transversely a distance beyond the absorbent intermediate layer and being mutually connected only on both sides of said intermediate layer within longitudinal areas along their outer edges, whereby the elastic band or thread means pull together the liquid-permeable outer layer which in turn pulls together sections of the liquidimpermeable layer around the edges of the absorbent intermediate layer.

2. A diaper according to claim 1, in which the elastic band or thread means are essentially parallel and extend in the transverse direction of the diaper.

3. A diaper according to claim 1, in which at least a pair of the elastic band or thread means are arranged so as to cross each other essentially at the longitudinal middle line of the diaper.

* * * * *